US010948338B2

(12) United States Patent
Delgado et al.

(10) Patent No.: US 10,948,338 B2
(45) Date of Patent: Mar. 16, 2021

(54) DIGITAL PRODUCT LABEL GENERATION USING MODULAR SCALE DEVICE

(71) Applicant: Walmart Apollo, LLC, Bentonville, AR (US)

(72) Inventors: Juan C. Delgado, Rogers, AR (US); Armon Nayeraini, Fayetteville, AR (US); Aaron Papera, Rogers, AR (US); Spencer Stokes, Springdale, AR (US); Lana Huckleberry, V, Gentry, AR (US); Samuel Hyman, Rogers, AR (US); Chad Smith, Rogers, AR (US); Timothy Choate, Bentonville, AR (US); Kurt William Robert Bessel, Mexico, NY (US); Eugene P. Sunday, Glen Ellyn, IL (US)

(73) Assignee: Walmart Apollo, LLC, Bentonville, AR (US)

( * ) Notice: Subject to any disclaimer, the term of this patent is extended or adjusted under 35 U.S.C. 154(b) by 178 days.

(21) Appl. No.: 16/231,393

(22) Filed: Dec. 22, 2018

(65) Prior Publication Data
US 2019/0234791 A1    Aug. 1, 2019

Related U.S. Application Data

(60) Provisional application No. 62/622,829, filed on Jan. 27, 2018.

(51) Int. Cl.
*G01G 23/37* (2006.01)
*H04W 4/35* (2018.01)
(Continued)

(52) U.S. Cl.
CPC ....... *G01G 19/4144* (2013.01); *G01G 19/415* (2013.01); *G01G 23/3735* (2013.01);
(Continued)

(58) Field of Classification Search
CPC . H04W 4/35; G01G 19/4144; G01G 23/3735; G01G 19/415; G06K 9/00671; G01N 33/0026
(Continued)

(56) References Cited

U.S. PATENT DOCUMENTS 3,986,012 A  * 10/1976  Loshbough .......... G01G 19/415
                                                   705/415
4,685,702 A  *  8/1987  Kazuharu ............. B41J 3/4075
                                                   283/81
(Continued)

FOREIGN PATENT DOCUMENTS

AU   007735875    *  7/1976  .......... G01G 19/415
CN   103983337 A      8/2014

OTHER PUBLICATIONS

Young, Lee W., "International Search Report and Written Opinion of the International Searching Authority", International Application No. PCT/US2018/067396, dated Apr. 1, 2019, 9 pages.
(Continued)

*Primary Examiner* — Jacques M Saint Surin

(57) ABSTRACT

The system and method described herein enable generating digital product labels for products that are valued by weight. Product identification data of a product is received via at least one of a user interface and a network interface. Value per weight data of the product is obtained from a product data store via the network interface. A weight value is determined from at least one scale device via the network interface and a product value is calculated based on the obtained value per weight data and the determined weight value. A digital product label is generated, including at least a portion of the product identification data and product value. The disclosure provides systems and methods that use multiple modular devices, such as the scale devices, printers, and product attribute collector devices, that provide flex-
(Continued)

ibility in organizing the system and reduced cost in initial setup and replacement of devices in the system.

20 Claims, 5 Drawing Sheets

(51) Int. Cl.
*G01N 33/00* (2006.01)
*G06K 9/00* (2006.01)
*G01G 19/415* (2006.01)
*G01G 19/414* (2006.01)

(52) U.S. Cl.
CPC ..... *G01N 33/0026* (2013.01); *G06K 9/00671* (2013.01); *H04W 4/35* (2018.02)

(58) Field of Classification Search
USPC ........................................ 177/25.15
See application file for complete search history.

(56) References Cited

U.S. PATENT DOCUMENTS

| | | |
|---|---|---|
| 5,635,906 A | 6/1997 | Joseph |
| 6,029,155 A | 2/2000 | Bass et al. |
| 6,526,828 B1 | 3/2003 | Dayan et al. |
| 7,597,254 B2 | 10/2009 | Miller et al. |
| 8,117,071 B1 | 2/2012 | Fitch et al. |
| 8,424,486 B2 | 4/2013 | Nielsen et al. |
| 8,822,848 B2 | 9/2014 | Meagher |
| 9,715,684 B2 | 7/2017 | Kobres |
| 2003/0078849 A1* | 4/2003 | Snyder .................. A47F 9/047 705/23 |
| 2006/0106742 A1* | 5/2006 | Bochicchio .......... G01G 19/083 705/414 |
| 2010/0181119 A1 | 7/2010 | Saigh et al. |
| 2011/0261995 A1* | 10/2011 | Cok ........................ G06F 16/50 382/100 |
| 2012/0217069 A1* | 8/2012 | Kawamura ............ G01G 21/28 177/25.13 |
| 2013/0126248 A1 | 5/2013 | Yamaguchi et al. |
| 2014/0289386 A1* | 9/2014 | Vatto ................ G06Q 10/06315 709/223 |

OTHER PUBLICATIONS

Samuel M. Yimenu et al., "Prediction of egg freshness during storage using electronic nose", Oxford Acedemic, https://academic.oup.com/ps/article/96/10/3733/4055767, captured Dec. 22, 2017, 181 pages.

Unknown, "Quality Assessment of Corn Silage using zNose", Electronic Sensor Technology Inc., YouTube video, https://www.youtube.com/watch?v=d2U-MIZWbtl, published Oct. 24, 2016.

* cited by examiner

DIGITAL PRODUCT LABEL GENERATION USING MODULAR SCALE DEVICE

BACKGROUND

In today's stores, modern scale devices are used for handling products that are valued by weight. The modern scales being used are not simple mechanical devices. They are intelligent, multi-media devices consisting of multiple integrated hardware peripherals driven by software, which is often proprietary. The modern scales include weight measuring devices, printers, multiple user interfaces, such as screens for use by an employee and a customer arranged on different parts of the scale. While such scales provide substantial functionality, the cost to replace a scale is high, and a single malfunctioning peripheral of the scale, such as a broken printer, can render the entire device unusable.

Further, the software that drives the many functions of the scale is tied to the scale and provides limited or no customizability, reducing the ability to create customized, efficient workflows that include the scale's functions. Also, software and hardware upgrades of the complex, modern scale devices can be costly when older models are no longer supported by manufacturers.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A computerized method for generating a digital product label is described. The method comprises receiving, by a processor, product identification data of a product via at least one of a user interface or a network interface. Value per weight data of the product is obtained from a product data store via a network interface. A weight value is determined from a scale device via a network interface and a product value is calculated based on the obtained value per weight data and the determined weight value. A digital product label is generated, including at least a portion of the product identification data and the product value.

Many of the attendant features will be more readily appreciated as the same becomes better understood by reference to the following detailed description considered in connection with the accompanying drawings.

BRIEF DESCRIPTION OF THE DRAWINGS

The present description will be better understood from the following detailed description read in light of the accompanying drawings, wherein:

Corresponding reference characters indicate corresponding parts throughout the drawings. In FIGS. 1 to 5, the systems are illustrated as schematic drawings.

The drawings may not be to scale.

DETAILED DESCRIPTION

The systems and methods described herein are configured for generating digital labels using modular scale devices. An orchestrator application receives product identification data of a product through a user interface, network interface, or the like. The orchestrator application obtains product value per weight data from a product data store via a network interface. A weight value is determined from a scale device via a network interface and a product value is calculated based on the obtained value per weight data and the determined weight value. The product value is used to generate a digital product label for the product, the label including at least a portion of the product identification data and the product value. The orchestrator application operates as a central controller of multiple modular devices, including the scale device. The modular devices may provide relatively simple functionality, and the data obtained from the modular devices is used by the orchestrator application to provide more complex functionality based on the combination of the various obtained data, such as generating a digital product label as described herein.

The described disclosure improves the complex computing systems used in stores to handle weighed products by reducing cost of operation and increasing customizability thereof. The use of modular devices to obtain and process data in order to provide functionality such as generating digital product labels decreases the costs of repair and/or replacement of individual devices of the system, reduces downtime of the system due to malfunction, and reduces reliance on proprietary devices and software. The described orchestrator application provides centralized control of a large network of modular devices that operate as a single cohesive device and that enables the design of efficient workflows that are manageable at an enterprise, store, or unit level.

Figure 1:
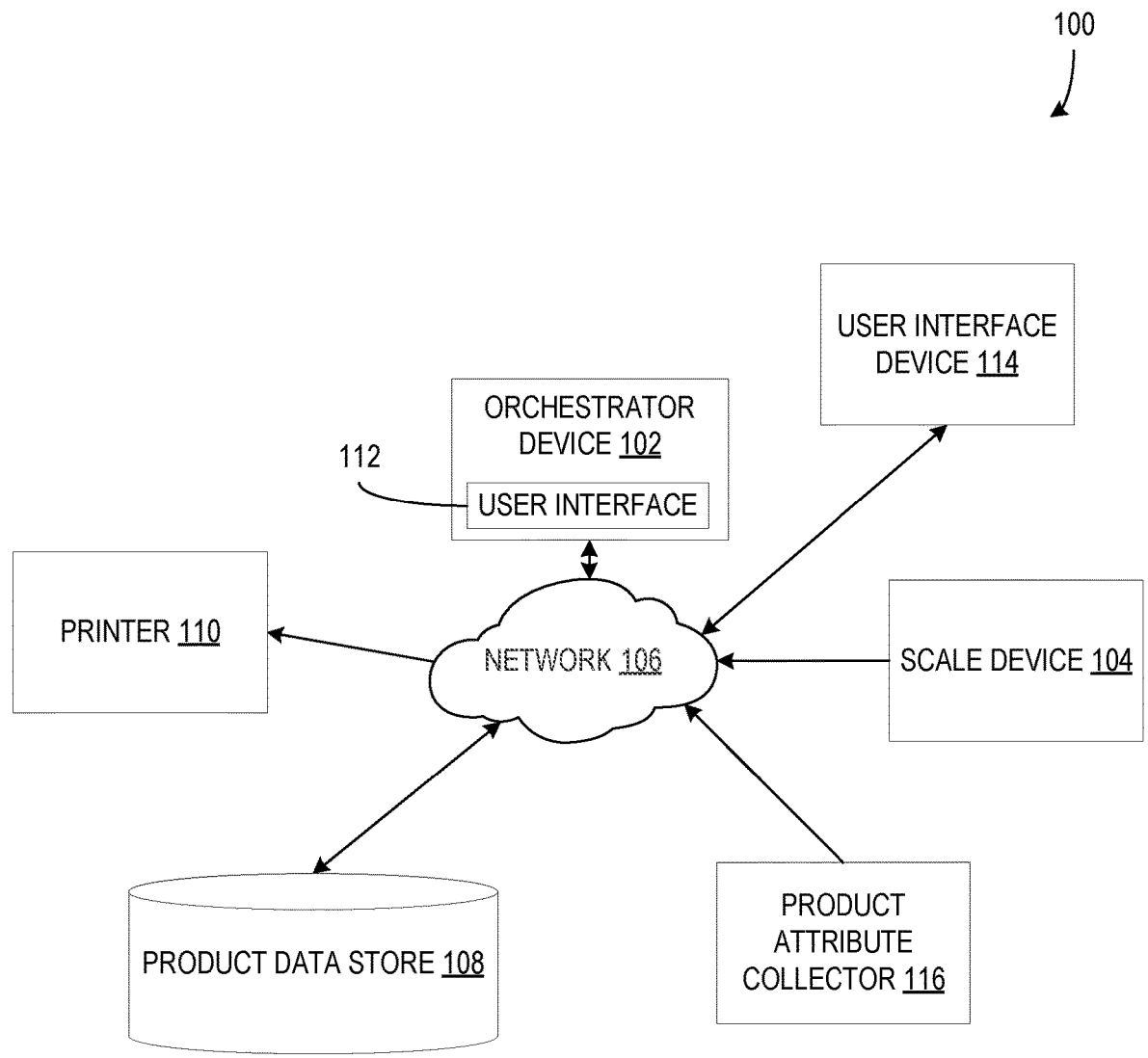
FIG. 1 is an exemplary block diagram illustrating a system configured for generating digital product labels based on data determined from a scale device according to an embodiment.

FIG. 1 is an exemplary block diagram illustrating a system 100 configured for generating digital product labels based on data determined from a scale device according to an embodiment. The system 100 includes an orchestrator device 102 that is configured to communicate with a scale device 104 via a network 106. Further, the system 100 components include a product data store 108, a printer 110, a user interface device 114, and a product attribute collector 116. The components of system 100 may be configured for communication with the orchestrator 102 via the network 106 and/or via other means of communication, such as communication directly between the orchestrator device 102 and the component. For instance, the orchestrator device 102 may include an optical interface, such as an infrared scanner or camera, that is configured to scan an interface of a component of system 100, such as the scale device 104, in order to obtain data from the component without using the network 106. Other known methods of device-to-device communication may be used without departing from the description herein.

The orchestrator device 102 is a computing device (e.g., a personal computer, a server device, a tablet, a mobile phone or smartphone, a wearable, etc.) that is configured to orchestrate, enable, and/or manage the operations described herein. The orchestrator device 102 may include a processor, memory, interfaces, and other hardware, firmware, and software components of computing apparatuses as would be understood by a person of ordinary skill in the art. The software included in the orchestrator device 102 is described below in the description of FIG. 2. The orchestrator device includes a user interface 112 that may enable a user of the orchestrator device 102 to provide input and communicate output to a user. The user interface 112 may include visual interface(s) such as a screen, lights, or other indicators, audio interfaces such as speakers and microphones, and/or mechanical or touch-based interfaces such as buttons, switches, keyboards, and/or touchscreens, gesture-recognition interfaces, and the like. The orchestrator device 102 is further configured for communication over the network 106 and may include one or more network interfaces as described below.

The scale device 104 is a device configured to measure a weight of an object or objects placed in or on the scale device 104. The scale device 104 may include a tray or other flat surface upon which objects to be weighed should be placed. The scale device 104 further includes one or more weight-measuring sensors, such as pressure sensors, spring-based sensors, or any other suitable sensor, that are linked to the tray or container of the scale device 104 to measure the weight of objects placed thereon. The weight-measuring sensors may be configured to provide weight data gathered by measuring the weight of objects placed on the scale device 104 to an output interface of the scale device 104. The scale device 104 may include a user interface, such as a display screen, and/or a network interface, such as a wired local area network (LAN) interface, a Wi-Fi network interface, a near field communication (NFC) interface, a BLUETOOTH® interface, etc. It should be understood that weight data gathered by the weight-measuring sensor(s) of the scale device 104 may be transformed from a raw form into a form that is understandable by users (e.g., a weight value and an associated unit of measure, such as pounds, ounces, kilograms, grams, etc.) and/or a form that is compatible with other devices (e.g., a barcode, such as a universal product code (UPC), a quick response (QR) code, a DIGIMARC® code, etc.). In some examples, the weight data collected by the scale device 104 is transmitted or otherwise provided to the orchestrator device 102 via the network 106. Alternatively, or additionally, the orchestrator device 102 may obtain weight data from the scale device 104 by scanning a barcode displayed by the scale device 104, receiving the weight data via an NFC or BLUETOOTH® communication, or receiving the weight data from the user interface 112 as inputted by a user who may be reading a user interface of the scale device 104 to transfer the weight data. It should be understood that the scale device 104 may be any device capable of measuring a weight value of an object and communicating the measured weight value to the orchestrator device 102 without departing from the description of the system 100. As used herein, a device capable of measuring a weight value of an object includes those devices authorized and/or certified by the National Conference of Weights and Measures, such as via the National Type Evaluation Program (NTEP) certification, and/or any local, regional, national, or other regulatory governing body. Further, in some examples, the system 100 may include multiple scale devices 104 with which the orchestrator device 102 may communicate.

The orchestrator device 102 may communicate with the product data store 108 to obtain and/or record product data during the process of generating digital product labels as described herein. The product data store 108 is configured to store product data, including product identification data, product value and/or product value per weight, product category, product attribute data, etc. The data stored by the product data store 108 may be based on location (e.g., the price of a product may be different depending on region or store location, etc.). In some examples, the product data store 108 is on a cloud server accessible via the network 106. Alternatively, the product data store 108 may be on a server that is locally located and/or specifically directed to a particular region and/or store, such that it is only accessible from the associated region or store via network 106.

In some examples, digital product labels generated by the orchestrator device 102 and associated components may be printed by the printer 110. The printer 110 may be printing device capable of receiving a digital product label from the orchestrator device 102, whether over the network 106 or through another means of communication (e.g. NFC, BLUETOOTH®, etc.), and printing the digital product label to paper or other similar physical media (e.g., adhesive label paper, etc.). The printer 110 may include a network interface that enables other devices (e.g., the orchestrator device 102, etc.) to send printing instructions and printable document data over the network 106. It should be understood that any network-capable printer 110 may be included in the system 100 and, in some cases, multiple printers 110 may be available in the system 100 for use by the orchestrator device 102 for printing digital product labels.

The user interface 112 and user interface device 114 may be used by the system 100 to communicate with users during the process of generating digital product labels. In some configurations of the system 100, the user interface 112 of the orchestrator device 102 is the only user interface used in the process. In some alternative examples, the orchestrator device 102 may be less accessible to users (e.g., the orchestrator device 102 functionality may be executed primarily on a server device, etc.) and a separate user interface device 114 may be necessary (e.g., a server-based orchestrator device 102 communicating with a user interface device 114 in the form of a user's smartphone or tablet, via an instance of an orchestrator application executing on the user interface device, etc.). It should be understood that the user interface 112 and user interface device 114 may be used separately or in combination in the system 100 without departing from the description.

The user interface 112 and user interface device 114 may be configured to receive product identification data as input from users. For instance, a user may enter a product identification code into the orchestrator device 102 by entering it on a touchscreen user interface 112. The product identification data entered may also be in the form of a name of the product and/or description of the product. The user interface 112 (or device 114) may be used to prompt a user to arrive at the correct product identification data by presenting a list of potential matches based on the data entered by the user.

Additionally, or alternatively, the user interface 112 may be used to direct a user to obtain the product identification data (e.g., directing the user to scan a barcode of the product with the camera of the user's smartphone, directing the user to take a photo of the product itself, or directing the user to place the product in a location where the identity of the product may be determined by other devices/sensors, etc.).

Further, the user interface 112 and/or user interface device 114 may be configured to display or otherwise provide generated digital labels to users. In some examples, digital labels may be presented on a screen user interface 112 of the orchestrator device or a screen user interface of the user interface device 114 to obtain confirmation of accuracy from the user. The confirmed digital label may be displayed to the user and/or other devices during a commercial transaction (e.g., the digital label may be provided to an associate or employee of the store and/or scanned by a scanning device to add the product described on the digital label to the transaction, etc.).

The user interface 112 and/or user interface device 114 may provide further functionality, such as receiving a weight value from a user, enabling general user interaction with applications of the orchestrator device 102, and the like. It should be understood that the user interface 112 and the user interface device 114 may provide user interface functionality as understood by a person of ordinary skill in the art without departing from the description herein. Further, the system 100 may include multiple user interface devices 114 in addition to the orchestrator device 102 without departing from the description.

In some examples, the system 100 includes one or more product attribute collectors 116. A product attribute collector 116 is a device configured to obtain one or more product attributes from a product and communicate the obtained attribute data to the orchestrator 102 for use in digital product label generation. In some examples, a product attribute collector 116 may collect raw product attribute data from an associated sensor and convert, format, or otherwise transform the raw product attribute data into one or more product attributes that are compatible for use by other components of the system 100. Alternatively, some or all of the transformation of raw product attribute data may be done by the orchestrator device 102 or other devices of the system 100. Product attribute collectors 116 may include, without limitation, chemical-sniffing devices, optical devices such as cameras and/or IR scanners, RFID sensors, and/or any other suitable sensor(s), for example. In some examples, product attribute collectors 116 may be a set of sensors, or an array of sensors, implemented within a weighing platform. In these examples, the sensor array may identify a shape and/or quantity of a given item disposed upon the weighing platform in addition to identifying a weight value. As one illustrative example, three green beans may be placed on a weighing platform, and the sensor array may detect and identify the quantity and item type using a number of algorithms, such as pattern recognition or pattern matching algorithms. The product attribute collectors' item identification in this illustrative example may be used to validate or verify a user selection of an item type (e.g. green beans) in addition to validating an item count and/or weight value for the selected item. In other examples, the product attribute data generated by the product attribute collectors 116 may be transmitted to and/or obtained by the orchestrator device 102 for analysis and determination of item type, item count, weight value, etc. As another example, optical scanners implemented within a weighing platform may scan or otherwise detect a product identifier or scannable code, such as a DIGIMARC® code, to identify the item type. The product attribute collectors 116 may be physically located and/or arranged near, adjacent to, and/or within the scale device 104 to enable the system 100 to obtain product attribute data at the same time that product weight data is obtained by the scale device 104. The product attribute data may be used by the orchestrator device 102 to determine an identity of the product and/or validate the identity of the product. The application of obtained product attribute data may include comparison to stored product attribute data as described in greater detail below.

The orchestrator device 102 and other components of the system 100 may communicate with each other over the network 106. It should be understood that network 106 may include one or more integrated or otherwise connected networks. The network 106 may include public and/or private networks, large-scale networks, such as the Internet, and/or relatively smaller intranets. The network 106 may be accessed via wired and/or wireless connections, using any and all network protocols as understood by a person of ordinary skill in the art.

Figure 2:
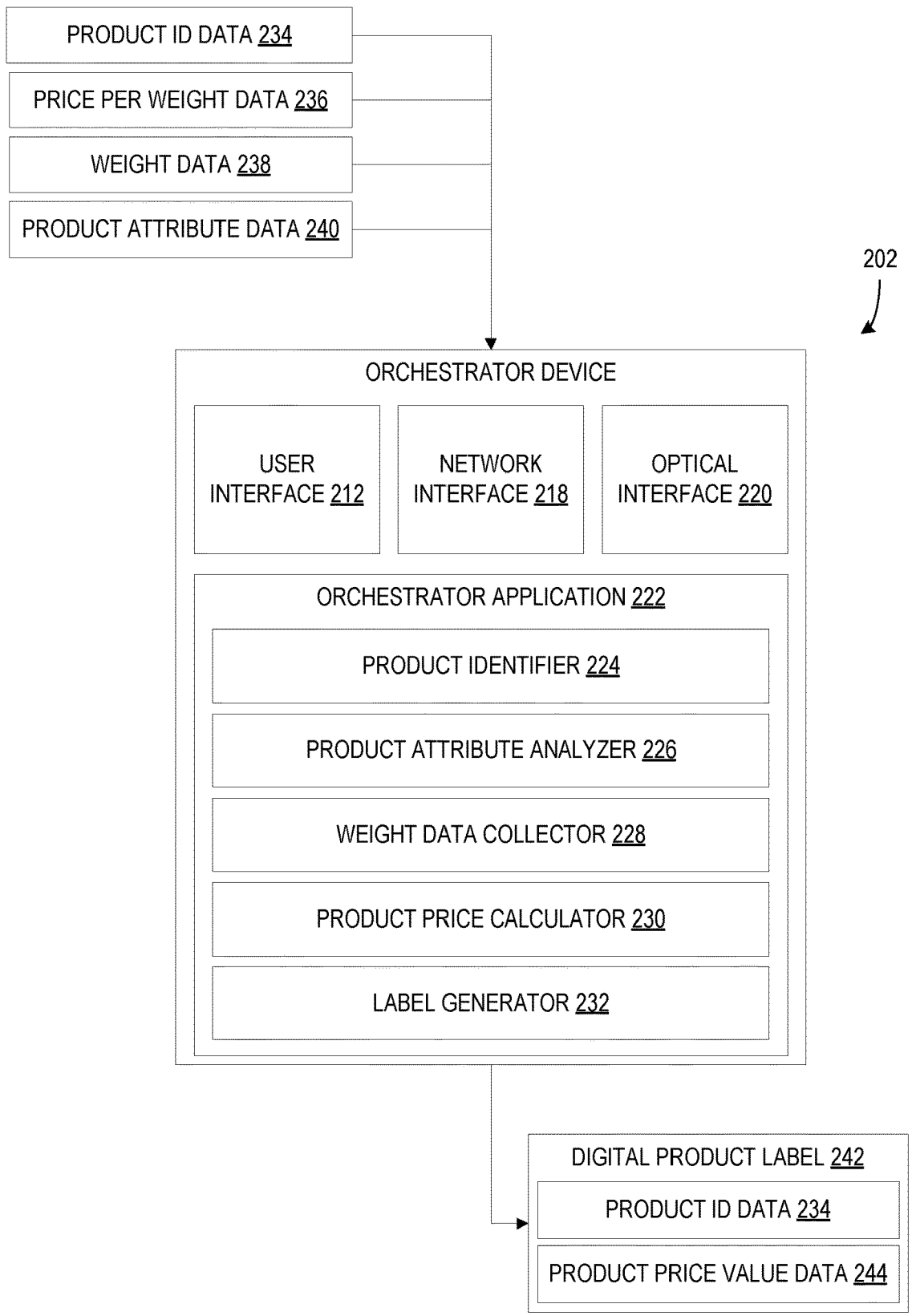
FIG. 2 is an exemplary block diagram illustrating an orchestrator device including an orchestrator application for generating digital product labels according to an embodiment.

FIG. 2 is an exemplary block diagram illustrating an orchestrator device 202 including an orchestrator application 222 for generating digital product labels 242 according to an embodiment. The orchestrator device 202 includes a user interface 212, a network interface 218, and an optical interface 220. In some examples, the orchestrator device 202 may include more, fewer, or different interfaces. The orchestrator application 222 is a software component of the orchestrator device 202 that configures the orchestrator device 202 to operate as described herein. The orchestrator application 222 includes software subcomponents, including a product identifier 224, a product attribute analyzer 226, a weight data collector 228, a product value calculator 230, and a label generator 232.

The orchestrator device 202 receives product identification (ID) data 234, value per weight data 236, weight data 238 and product attribute data 240 as input data as described herein. The orchestrator device 202 generates and may output a digital product label 242, including product ID data 234 and product value data 244, based on the processing, analyzing, and/or transformation of the data received as input data.

The interfaces of the orchestrator device 202 provide a variety of ways to for the orchestrator device 202 to receive input data and to send or provide output data. The user interface 212 may include a variety of types of user interfaces as described above with respect to user interface 112 in system 100 of FIG. 1. The network interface 218 may include hardware and software components that enable the orchestrator device 202 and applications on the orchestrator device 202 (e.g., the orchestrator application 222, etc.) to communicate with other devices using network protocols (e.g., wired protocols such as Ethernet-based protocols, wireless protocols such as Wi-Fi protocol, cellular data protocol, NFC protocol, BLUETOOTH® protocol, radio frequency identification-based (RFID) protocols, etc.). The optical interface 220 may include hardware and software components that enable the orchestrator device 202 to receive in compatible optical formats. The optical interface 220 may include a camera, infrared scanner, or the like.

The product identifier 224 of the orchestrator application 222 receives the product ID data 234, identifies the product or products associated with the product ID data 234, and retrieves or otherwise obtains data associated with the product or products identified by the product ID data 234. The product identifier 224 may be configured to request and receive product ID data 234 via the user interface 212, the network interface 218, the optical interface 220, or a combination thereof. For instance, the product identifier 224 may cause the user interface 212 to display a prompt instructing a user to enter a product ID code and then receive, via the user interface 212, any product ID code provided by the user. Alternatively, or additionally, the product identifier 224 may provide instructions to users to scan a barcode of a product using the optical interface 220 to obtain the product ID data 234.

The product identifier 224 may communicate with a product data store (e.g., product data store 108, etc.) to obtain product data based on the product ID data 234. For instance, the product identifier 224 may send a query including the product ID data 234 to the product data store via the network interface 218. If the product ID data 234 includes a unique product code or index, the product data store may retrieve and provide product data associated with the unique product code or index. Alternatively, if the product ID data 234 includes non-unique data, such as a product name or associated keyword, the results of the query to the product data store may include product data associated with multiple products that match the product ID data 234. The product identifier 224 may prompt a user to select the product from the multiple product results that most closely matches the product to be identified.

When the product associated with the product ID data 234 is identified, the product identifier 224 retrieves value per weight data 236 associated with the product from the product data store via the network interface 218. Other product data may also be retrieved (e.g., value per unit data if the product is not priced by weight, sale or discount data associated with the product, a product category, nutrition data of the product, supply chain data associated with the product, product origin data, product attribute data 240 as described below, etc.).

In some examples, the product attribute analyzer 226 is a software component of the orchestrator application 222 that analyzes product attribute data 240 to aid in the identification of the product and/or validate the identification of the product. The product attribute analyzer 226 may obtain the product attribute data 240 from product attribute collector devices (e.g., product attribute collector 116, etc.). The product attribute data 240 may be obtained via the network interface 218 when the product attribute collector devices are compatible with network communication (e.g., a chemical-sniffing device that is connected to a Wi-Fi network and can be accessed by other devices over the Wi-Fi network and/or over the Internet, etc.). Alternatively, or additionally, the product attribute data 240 may be obtained via the optical interface (e.g., scanning a QR code that includes the product attribute data 240 in the form of chemical signature data of the product displayed on a chemical-sniffing device, taking a photo of the product using a camera of the orchestrator device 202 to obtain optical attribute data of the product, etc.).

Further, the product attribute analyzer 226 may retrieve stored product attribute patterns that may be associated with the product for comparison to the obtained product attribute data 240. The product attribute patterns may be stored on a product data store or other associated data store, which may be accessed via the network interface 218. In some examples, the product attribute data 240 may be used for the identification of the product. In that case, the product attribute data 240 may be used by the product attribute analyzer 226 and/or a server on which the product attribute patterns are stored for comparison to the product attribute patterns to find a closest match or matches among the possible products. Alternatively, or additionally, the product attribute data 240 may be used to validate the identification of the product, wherein the product attribute data 240 is compared to product attribute patterns associated with the identified product to determine the accuracy of the identification. In both product identification and product identity validation, the comparison of the product attribute data 240 and the stored product attribute patterns may be based on defined match thresholds, which may be percentage-based, based on a total number of matching attribute data values, range-based, etc. For instance, the product attribute data 240 may include an optical pattern, shape, size, density, and/or color of the product which are compared to the stored product optical attribute patterns of products in the product data store to identify products attribute patterns that are a match, or a substantially similar match, to the obtained product attribute data 240. In some examples, match thresholds may be configurable and may be product-specific. For examples, the color and density of a produce item may change over time and/or due to exposure to various conditions, which may provide a range of color and/or density measurements for a match threshold. Alternatively, or additionally, the product attribute data may include a chemical signature of the product, including a plurality of data points indicating levels of chemicals present in the chemical signature. The obtained chemical signature may be compared to a stored chemical signature pattern of the identified product and, if 10 or more data points of the chemical signature match the stored chemical signature pattern, the identification of the product is validated.

In some examples, the product identifier 224 and product attribute analyzer 226 may function together to identify the product. For instance, a product may be placed onto a scale and an associated camera, or other sensor, may capture optical data of the product. The product attribute analyzer 226 analyzes the captured optical data and determines a product that is a match based on a comparison to stored product attribute data patterns. The product ID data 234 of the determined product may be provided to the product identifier 224, which may retrieve associated product data as described above. In the examples described herein, the plurality of data points obtained and/or captured by the product attribute collectors (sensors) may be joined together to identify a sub-set of candidate products to display to a user for selection and/or verification of a product type. In these examples, options presented to a user interface display, such as via the orchestrator device, may be the sub-set of candidate products identified based on the obtained product attribute data.

Alternatively, or additionally, the product identifier 224 may identify the product based on other methods of obtaining the product ID data 234 and the product attribute analyzer 226 is configured to validate the identification of the product. For instance, a product may be placed onto a scale and an associated chemical-sniffing device may obtain a chemical signature of the product. The product attribute analyzer 226 analyzes the chemical signature by comparing it to the stored chemical signature pattern of the identified product. If the chemical signature and stored chemical signature pattern match based on a defined threshold, the identification of the product is validated and the process of generating a label continues. If the chemical signature and stored chemical signature pattern do not match based on the defined threshold, the process may be paused and/or cancelled. The user may be prompted to re-initiate the identification of the product and/or an associate or employee may be prompted to aid the user in generating an accurate digital label for the product.

The weight data collector 228 of the orchestrator application 222 is a software component configured to obtain weight data 238 from a scale device (e.g., scale device 104, etc.) via user interface 212, network interface 218, or optical interface 220. The weight data collector 228 may cause the orchestrator device 202 to request weight data 238 from a scale device over the network 218 or to listen for and receive weight data 238 from the scale device via the network interface 218. Alternatively, or additionally, the weight data collector 228 may cause the optical interface 220 to capture a displayed number or code from the scale device, or cause the user interface 212 to prompt the user to enter weight data 238 manually to the user interface 212.

The weight data 238 may include one or more weight values, including a number of units and a specific unit of measure (e.g., 2.5 pounds, 8 ounces, 0.85 kilograms, 150 grams, etc.). Based on the format of the weight data 238, the weight data collector 228 may convert the weight data 238 to other units of measure or otherwise transform the weight data 238 (e.g., convert the weight data 238 to units of measure to match the value per weight data 236 of the product, decode encoded weight data 238, etc.).

The product value calculator 230 is a software component of the orchestrator application 222 that obtains the value per weight data 236 of the product from the product identifier 224 and the weight data 238 from the weight data collector 228 and then calculates the product value data 244. The product value calculator 230 may multiply the value per weight data 236 by the weight data 238 to obtain the product value data. In some examples, the product value calculator confirms that the units of measure of the value per weight data 236 and the weight data 238 match prior to calculating the product value. If the units of measure of the two data points do not match, the product value calculator 230 may convert one or both of the value per weight data 236 and the weight data 238 to matching units of measure. The product value data 244 includes the calculated product value and, in some examples, further data points associated with the product value, such as an amount saved due to a current sale or discount on the product.

The label generator 232 is a software component of the orchestrator application 222 that obtains data from other software components, including the product ID data 234 and product value data 244, and generates a digital product label 242 based on the obtained data. The label generator 232 may include a defined label template that determines the format of generated digital product labels 242, such that generation of the digital product label 242 includes inserting product ID data 234 and product value data 244 into the label template. In some examples, the digital product label 242 may further include the value per weight data 236, the weight data 238, and/or other data associated with the product, such as data obtained by the product identifier 224 as described above.

In some examples, the digital product label 242 is generated in a format that is printable (e.g., printable document format (PDF), etc.). The label generator 232 or the orchestrator application 222 generally may be configured to send the digital product label 242 to one or more associated printer devices (e.g., printer 110, etc.). Further, the digital product label 242 may include the product ID data 234, product value data 244 and other data in human-readable format. Additionally, or alternatively, the digital product label 242 may include a barcode (e.g., UPC, QR code, etc.) that includes some or all of the information of the digital product label 242, such that the digital product label is scannable by barcode scanners, cameras, or the like. For instance, the orchestrator device 202 may be a tablet computing device arranged next to a scale device that a customer interacts with to obtain a digital product label 242 for products placed on the scale. The orchestrator device 202 may display a generated digital product label 242 on a user interface 212 and the customer may scan a QR code of the displayed digital product label 242 using a smartphone to add the product to a digital shopping cart stored on the smartphone.

The digital product label 242 may include data associate with one or more products, such that a user may weigh several products in a sequence and obtain a single digital product label 242 that includes all of the products of the sequence. For example, a customer may want to purchase multiple products in varying quantities using the same label and/or package, such as purchasing an assortment of deli meats at a deli counter. The deli counter may use an orchestrator device, such as orchestrator device 202, to communicate with one or more scale devices capable of interfacing with the orchestrator device, and a printer device to produce the label. A first deli meat product may be selected and a portion of the first selection measured on the scale. A code associated with the selected deli meat product may be obtained by the orchestrator device. The code may be obtained via data input, such as a user entering a code or selecting the deli meat product from a menu, a barcode scan associated with the deli meat product, or the like. In some examples, other associated devices may be used to identify the selected deli meats. For instance, product identifiers on each package of deli meat product may detect the removal of the product from the display and/or the addition of that package to a scale device, and communicate that removal and/or addition to the orchestrator device, which may, in turn, prompt for user confirmation that the detected deli meat product is the correct product identified. Product identifiers may include, without limitation, RFID tags, DIGIMARC® codes, barcodes, QR codes, or any other scannable code, for example.

The orchestrator device obtains weight values from the one or more scale devices as described herein. In this example, multiple deli meat products may be weighed in sequence on the same scale and the orchestrator device may be configured to "tare" the received weight values between the weighing of each product to account for the weight of the product already present on the scale. Alternatively, or additionally, the multiple deli meat products may be weighed on more than one scale device, selecting the scale to use for each product from the user interface of the orchestrator device.

The orchestrator device may obtain the value per weight data for each deli meat product as they are identified by the user and/or system as described herein. Upon calculating the product values for each product, the digital product label 242 including product data for each of the multiple deli meat products may be generated. In some examples, the digital product label 242 is a computer file that is compatible with being printed to paper or another physical label medium. The data of the digital product label 242 may also be converted into a barcode format, such as a QR code, for scanning by capable devices. In other examples, the digital product label 242 may be stored in a data store location accessible by other computing devices and an associated barcode and/or uniform resource locator (URL) or the like may be generated that directs computing devices to access and/or download the stored digital product label 242.

In some examples, the generated digital product label 242 may be interactive, enabling a user to observe the list of products and prices and select specific products to view additional information, such as additional description of the product, nutritional information about the product, etc. The digital product label 242 may be viewable from within the orchestrator application and/or other compatible applications, such as web browsers. Further, the digital product label 242 may enable users to add products, edit products, remove products, or otherwise edit the digital product label 242 prior to initiating a transaction for the products.

Figure 3:
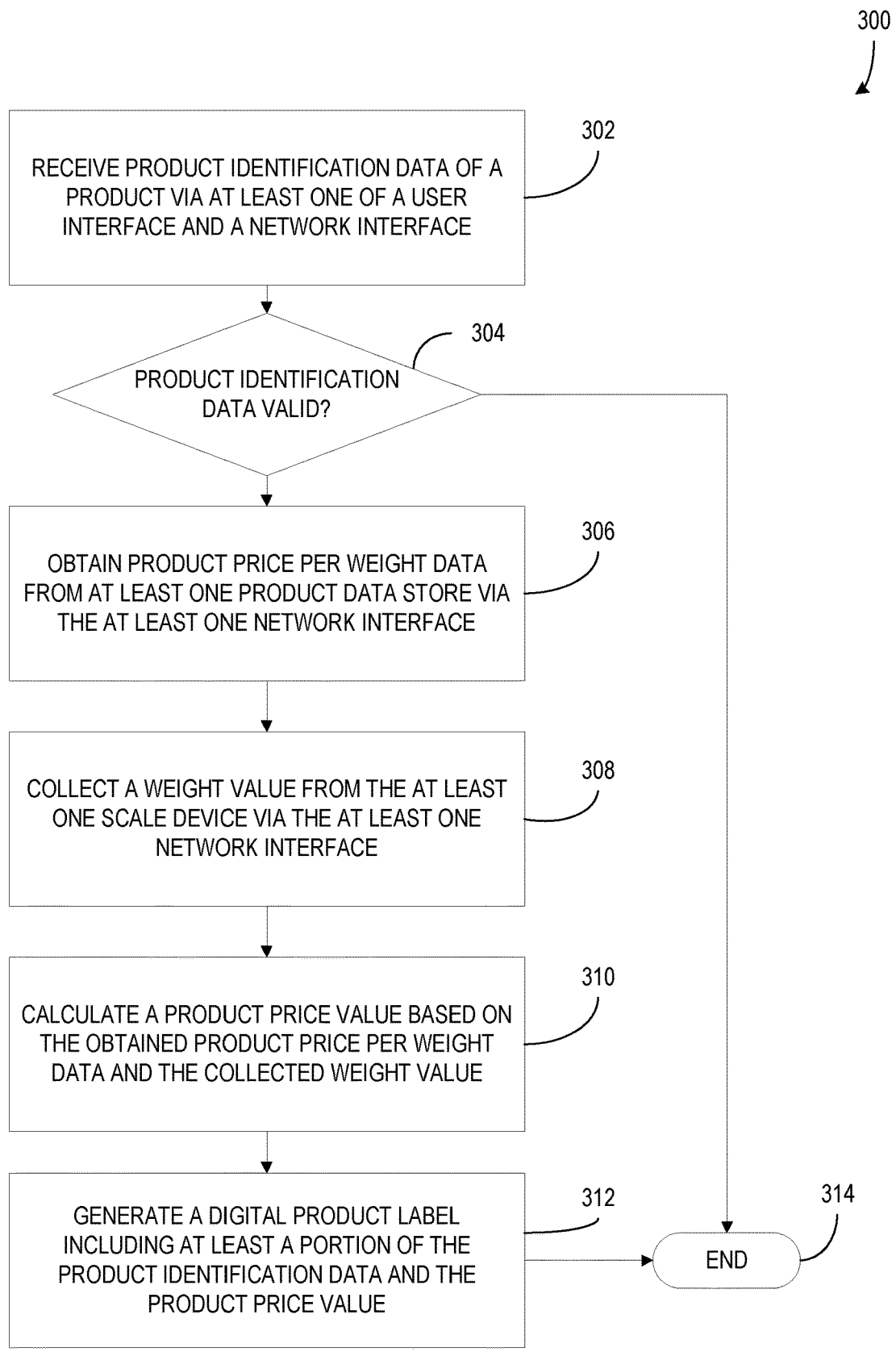
FIG. 3 is an exemplary flow chart illustrating a process of generating a digital product label based on product data and a determined weight value according to an embodiment.

FIG. 3 is an exemplary flow chart 300 illustrating a process of generating a digital product label based on product data and a determined weight value according to an embodiment. The process of flow chart 300 may be implemented on a computing device (e.g., orchestrator devices 102, 202, etc.) and/or on a system of devices (e.g., system 100, etc.). The steps or sub processes of the process may be executed by one or more processors based on computer-executable instructions on computer memory.

At operation 302, product identification data (e.g., product ID data 234, etc.) of a product is received by a processor via at least one of a user interface (e.g., user interface 212, etc.) and a network interface (e.g., network interface 218, etc.). The product identification data may be product ID data 234 as described above and it may include, for instance, a unique product code, a product name, a keyword associated with the product, a product category, and/or product attribute data. The product identification data may be received via user interface as a result of entry of the data by a user or it may be received via a network interface from one or more other devices (e.g., product attribute collector device 116, user interface device 114, etc.).

At operation 304, the product identification data may be validated for accuracy. In some examples, product attribute data (e.g., product attribute data 240, etc.) is used to validate the product identification data via a product attribute analyzer (e.g., product attribute analyzer 226, etc.) as described above. If the product identification data is found to be accurate, the process proceeds to operation 306. If the product identification data is found to be inaccurate, the process ends at operation 314. In some examples, finding product identification data to be invalid may cause a device or devices of the system to prompt a user to address the issue, cause the process to be reset, or otherwise respond to the invalid product identification data.

In alternative examples, the product identification data may be assumed valid (e.g., the product identification value is provided by an associate or employee, etc.), such that the validation at operation 304 is automatic.

At operation 306, the product value per weight data (e.g., value per weight data 236, etc.) of the product is obtained from at least one product data store (e.g., product data store 108, etc.) via the at least one network interface (e.g., network interface 218, etc.). In some examples, the obtained product value per weight data may include data as described above with respect to the value per weight data 238 obtained by the product identifier 224. In some alternative examples, the value per weight data may be obtained from the product data store prior to receiving the product identification data and stored by the computing device upon which the process is being executed (e.g., the a user's smartphone running an orchestrator application 222 may cache a list of product value per weight data associated with a region or store upon entering the region or store or upon the orchestrator application 222 identifying that the smartphone is in the region or store based on global positioning system (GPS) technology or local network detection, etc.).

At operation 308, a weight value (e.g., weight data 238, etc.) is determined from at least one scale device (e.g., scale device 104, etc.) via the at least one network interface (e.g., network interface 218, etc.). Determining a weight value may include collecting raw data from the at least one scale device and converting, processing, or otherwise transforming the raw data to make it usable by other components of the system. In an example, the at least one scale device is connected to a network such that the current weight value detected by the scale device is accessible to other devices over the network. In alternative examples, the weight value may be obtained via a user interface, optical interface, or other like interfaces as described above with respect to the weight data collector 228.

At operation 310, a product value (e.g., product value data, etc.) is calculated based on the obtained product value per weight data and the determined weight value. Calculation may include multiplying the value per weight of the product by the weight value and it may also include converting or otherwise transforming one or both of the value per weight data and the weight value for compatibility as described above with respect to the product value calculator 230.

At operation 312, a digital product label (e.g., digital product label 242, etc.) is generated, including at least a portion of the product identification data and the product value. In some examples, the digital product label may include data in addition to the product identification data and the product value, as described above with respect to the label generator 232. For instance, a generated digital product label may include a list of the names of multiple products, product values for each of the multiple products, a sum total of the product values, an amount saved based on sales, discounts, or coupon use, a barcode such that the product label can be scanned to obtain the label information, etc. At operation 314, the process ends.

In some examples, after the digital label is generated, it may be transmitted to or obtained by another computing device (e.g., a consumer's smartphone, an employee's mobile device or tablet, etc.), it may be sent to a network printer for printing (e.g. printer 110, etc.), and/or it may be used to initiate and/or complete a purchase transaction for the products shown on the digital label. The digital label may be used in a transaction on a customer's smartphone or tablet, on an associate or employee's tablet or device, or on a point-of-sale terminal.

Figure 4:
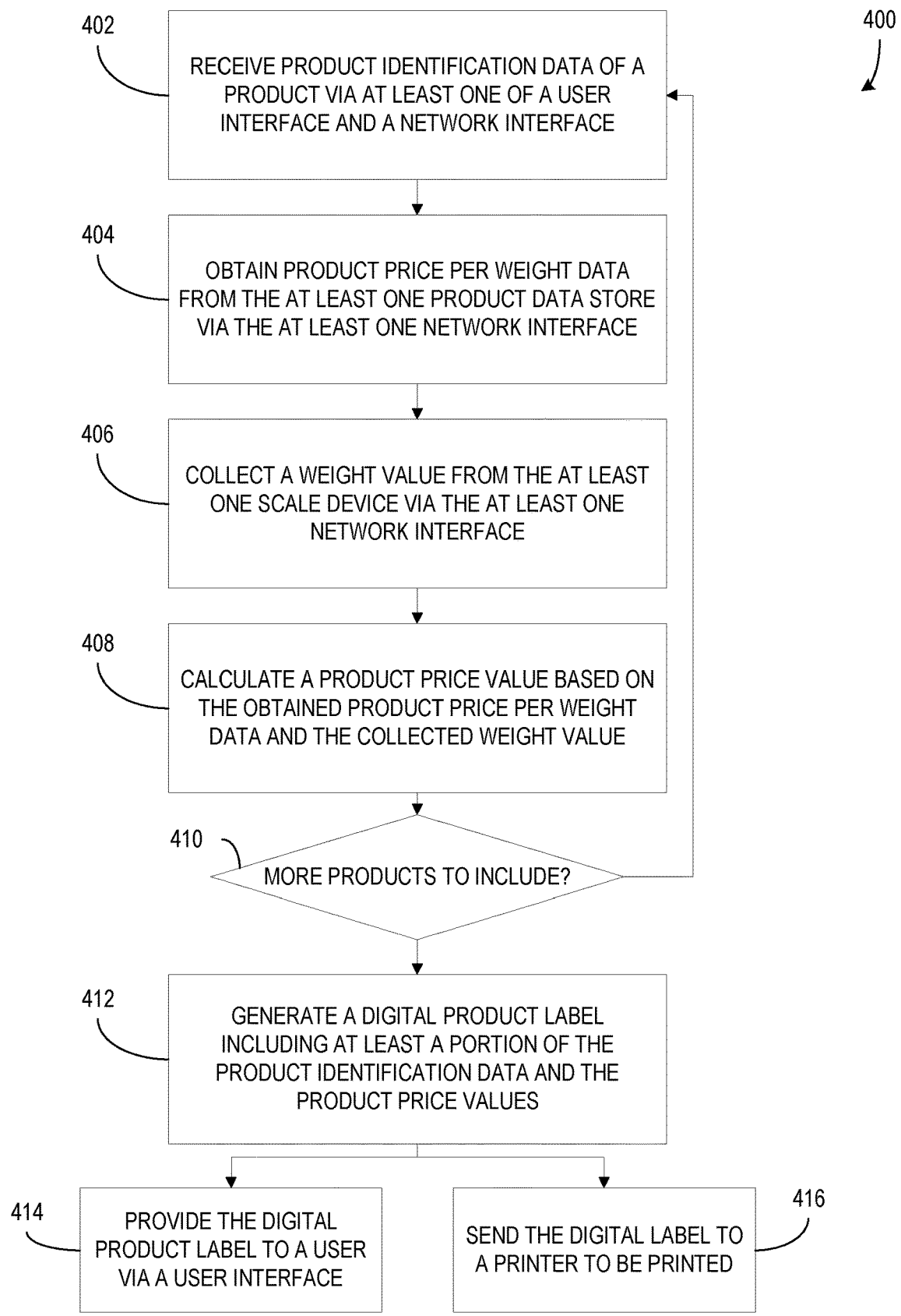
FIG. 4 is an exemplary flow chart illustrating a process of generating a digital product label for multiple products based on product data and sequentially determined weight values according to an embodiment.

FIG. 4 is an exemplary flow chart 400 illustrating a process of generating a digital product label for multiple products based on product data and sequentially determined weight values according to an embodiment. The process of flow chart 400 may be implemented on a computing device (e.g., orchestrator devices 102, 202, etc.) and/or on a system of devices (e.g., system 100, etc.). The steps or sub processes of the process may be executed by one or more processors based on computer-executable instructions on computer memory.

The operations from 402-408 include receiving product identification data, obtaining product value per weight, determining a weight value, and calculating a product value based on the obtained product value per weight data and the determined weight value as described above with respect to operations 302 and 306-310 of FIG. 3. At operation 410, the executing device determines whether there are more products to include on the digital product label to be generated. The determination may include generating a user prompt to enter additional product identification data or choose to complete the digital label. Alternatively, the total number of products to be included on the digital label may have been received prior to the process, such that the next product identification data is automatically requested when products remain to be included. In other examples, the presence of more products may be detected based on changes in the available weight value from the scale device being used during the process (e.g., a user may stack additional products onto the scale throughout the process and the orchestrator application may monitor the weight value of the scale, enabling changes in the weight to be identified, etc.). Additionally, or alternatively, a timeout threshold may be defined, such that, when the time that has passed since the last addition of a product or related interaction exceeds the timeout threshold, the process of adding products is determined to be complete and the label generation process continues as described below. The timeout threshold may be defined with a default value and it may also be configurable by a user of the orchestrator device and/or orchestrator application.

If there are more products to include at operation 410, the process returns to operation 402 to receive the product identification data of the next product. However, if there are no more products to include at operation 410, a digital product label including at least a portion of the product identification data and the product values are generated at operation 412. As described above the digital product label may include a list of the multiple products for which the label was generated, as well as value data and other associated data.

At operation 414, the generated digital product label may be provided to a user via a user interface. The user interface may be a user interface of the orchestrator device (e.g., user interface 112, 212, etc.) or it may be a user interface on a separate device (e.g., on user interface device 114, etc.). For instance, if the orchestrator device is a terminal at a meat counter that is controlled by associates or employees, the generated digital product label may be provided to a customer by displaying the digital product label on a screen interface of the terminal and/or by sending the digital product label to the customer's smartphone via a network interface. Alternatively, or additionally, the digital product label may be displayed on a screen interface in a scannable format, such as a barcode or QR code, such that user can obtain the digital product label by scanning the scannable format digital product label using a smartphone or other mobile device. Further, as described above, a link to a network location of a generated digital product label may be displayed to the customer in a scannable format such that the customer may access the digital product label at the linked network location by scanning the displayed link.

Alternatively, or additionally, at operation 416, the generated digital product label may be sent to or obtained by a printer (e.g., printer 110, etc.) to be printed. For instance, in the above example, the terminal at the meat counter may be in network communication with a label printer device nearby and, when the digital product label is generated, a user may select to have the label printed by the label printer device. The terminal sends the digital product label to the label printer and the label printer prints it. The printed label may then be taped or adhered to a package containing the product, or otherwise attached to the product.

Additional Example Scenarios

Aspects of the disclosure enable various additional scenarios. In one example, a product display may include associated and/or embedded sensors or sensor arrays configured for detecting and/or capturing weight values at the display. For example, a product display may be a produce bin for apples, and weight sensors associated with the produce bin may detect removal of an apple from the bin based on a decrease in weight. In this example, a weight range per-item may be known and/or preconfigured such that a calculated difference in a detected weight before and after detection of a decrease may be used to identify a number of items removed from the display. This data may be transmitted as product attribute data to an orchestrator device, for example.

In another example, a product display may include associated sensors or sensor arrays configured for detecting and/or scanning product identifiers, such as scannable codes or RFID tags. In this example, product removal may be detected via the sensors or sensor arrays and communicated to the orchestrator device, for example.

Another illustrative example may include a sample kiosk with product samples and associated sensor or other devices for obtaining a user selection directed at obtaining a purchase order for the product. Upon receiving a user selection at the sample kiosk, the system may generate a notification of the user selection, including product attribute data for the associated product at the sample kiosk, for output to a product order fulfillment area. The orchestrator device may also add the user selection to a virtual cart associated with the user based on the notification of the user selection. The product order may be fulfilled for the product the user sampled. For example, a user device at the order fulfillment area may obtain the user selection and an associate may fill the order for user pickup at the order fulfillment area. The orchestrator device may obtain the weight value for the order fulfillment from a scale device associated with the order fulfillment area, and may obtain value per item weight information as described herein, in order to generate a digital label for the ordered product.

In an example, an associate working behind in a meat department of a store is equipped with a table that runs an orchestrator application that is in network communication with peripheral devices throughout the meat department. A customer requests a pound of ground beef. The associate enters a product code for ground beef into the tablet, and then places about a pound of ground beef onto a nearby scale device. The orchestrator application retrieves product data associated with the ground beef from a product data store, including a value per weight value of $4.99 per pound. When the associate has the ground beef on the scale, the associate selects an identifier of the scale on the screen of the tablet and the orchestrator application obtains the weight value of the ground beef from the scale over a network connection. The orchestrator application applies the retrieved value per weight value of the ground beef to the obtained weight value and calculates a product value of the ground beef. A user interface device that is facing the customer displays the product value to the customer and the associate asks if the amount of ground beef is satisfactory. When the customer agrees that it is correct, the associate instructs the orchestrator application to generate a digital product label and send it to a nearby label printer. The orchestrator application generates a digital product label that includes "Ground Beef", the weight value of the ground beef, the $4.99 value per weight value, and the product value of the ground beef. The label also includes a barcode that is scannable by other devices to obtain the information of the digital product label. Once the label is printed, the associate wraps up the ground beef, attaches the printed label, and hands the package to the customer.

In a related example, another customer approaches the counter and requests a pound of ground pork sausage and a pound of ground beef, stating that they can be wrapped together. Once the associate has prepared about a pound of ground beef on the scale and obtained a product value for the ground beef as described above, the associate selects an option on the table to add another product. The associate then enters a product code for the ground pork sausage and adds about a pound of ground pork sausage to the scale. The orchestrator application obtains the value per weight value associated with ground pork sausage from the product data store and the new weight value of the scale. The orchestrator application tares the new weight value to remove the weight of the ground beef and calculates a product value for the ground pork sausage. The customer is prompted confirm that the amounts for both products are acceptable and, upon receiving the customer's approval, the associate instructs the orchestrator application to generate the digital label. The customer requests the label in digital format, so the associate causes the digital label to be displayed on the customer-facing screen interface, including a QR code scannable by the customer's smartphone. The customer scans the digital label and it is added to the customer's digital shopping cart application. The associate provides a package of the customer's requested meat to the customer.

In another example, the customer's smartphone includes the orchestrator application. The customer is shopping in the produce section. The customer selects a bunch of bananas and sets them on a nearby scale to determine their weight. The customer attempts to enter a product code for bananas, but accidentally enters the code for strawberries instead. The orchestrator application attempts to validate the customer's product identification by retrieving optical attribute data of the bananas from a camera arranged near the scale and optical attribute data patterns associated with strawberries from the product data store. The optical attribute data and the optical attribute data patterns do not match, as strawberries and bananas are substantially different shapes and colors. The orchestrator application prompts the user to reconsider the identification by displaying "Are you sure your product is strawberries?". The user realizes the mistake and chooses to reenter the product code, making sure to enter the correct code for bananas. The orchestrator application validates the product identification based on newly obtained optical attribute data and proceeds with the digital label generation process. The value per weight of bananas is obtained from a product data store and a weight value is obtained from the scale on which the bananas are placed. The orchestrator application may determine which scale and/or camera device to communicate with based on the proximity of the user's smartphone with the devices or by instructing the user to bring the smartphone close to the side of the scale, enabling a transfer of a scale identifier via NFC. The product value is calculated by the orchestrator application and a digital label is generated therefrom. The generated digital label is displayed to the customer on the smartphone and the customer is prompted to confirm the accuracy of the label. The customer confirms that the label is accurate, and then chooses to initiate the purchase of the bananas using the digital label. The orchestrator application communicates with an associated shopping application to initiate the transaction, enabling the customer to make the purchase immediately.

Exemplary Operating Environment

Figure 5:
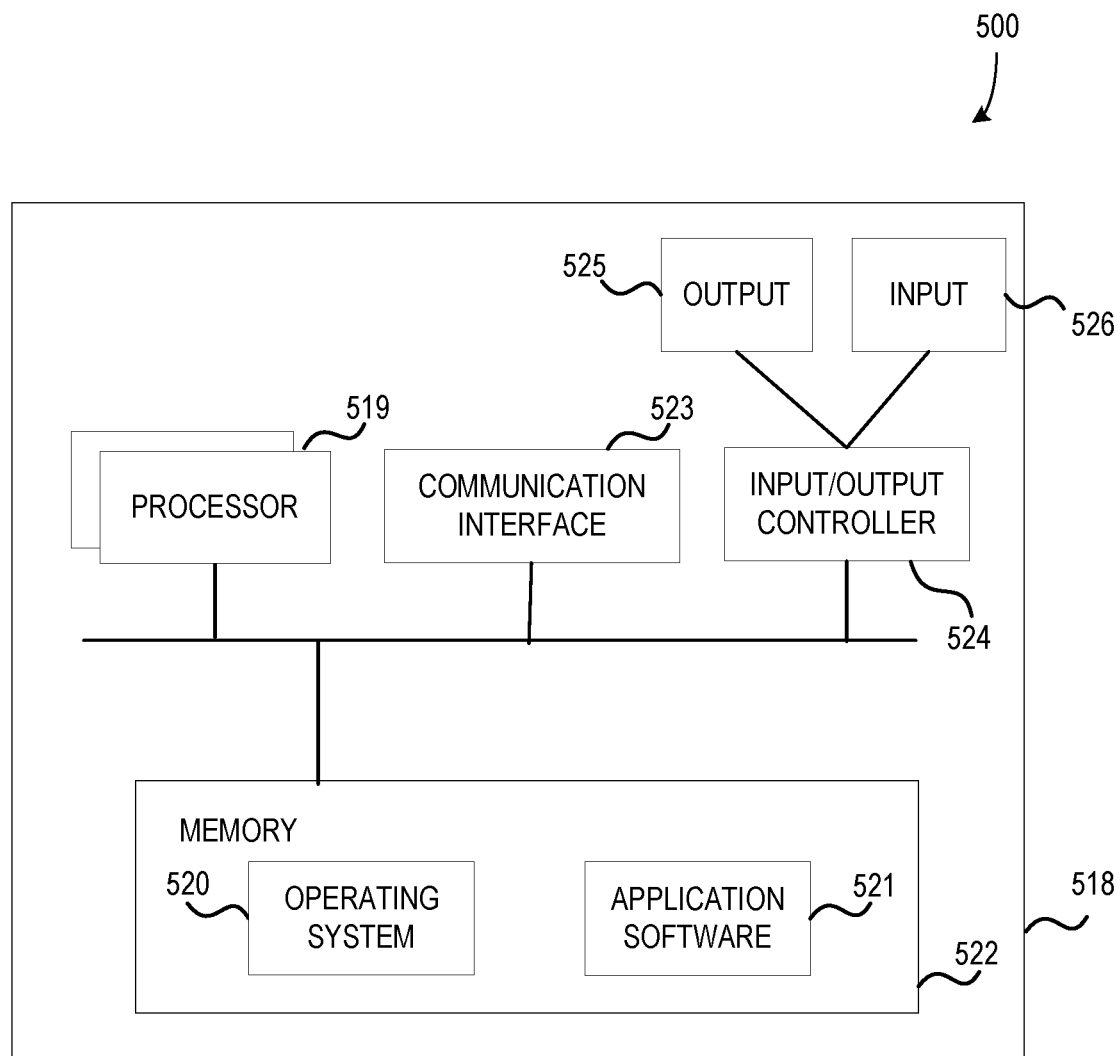
FIG. 5 illustrates a computing apparatus according to an embodiment as a functional block diagram.

The present disclosure is operable with a computing apparatus according to an embodiment as a functional block diagram 500 in FIG. 5. In an embodiment, components of a computing apparatus 518 may be implemented as a part of an electronic device according to one or more embodiments described in this specification. The computing apparatus 518 comprises one or more processors 519 which may be microprocessors, controllers or any other suitable type of processors for processing computer executable instructions to control the operation of the electronic device. Platform software comprising an operating system 520 or any other suitable platform software may be provided on the apparatus 518 to enable application software 521 to be executed on the device. According to an embodiment, identifying a product, obtaining value per weight data and weight data associated with the product, and generating a digital product label including product ID data and product value data of the product as described herein may be accomplished by software.

Computer executable instructions may be provided using any computer-readable media that are accessible by the computing apparatus 518. Computer-readable media may include, for example, computer storage media such as a memory 522 and communications media. Computer storage media, such as a memory 522, include volatile and non-volatile, removable and non-removable media implemented in any method or technology for storage of information such as computer readable instructions, data structures, program modules or the like. Computer storage media include, but are not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing apparatus. In contrast, communication media may embody computer readable instructions, data structures, program modules, or the like in a modulated data signal, such as a carrier wave, or other transport mechanism. As defined herein, computer storage media do not include communication media. Therefore, a computer storage medium should not be interpreted to be a propagating signal per se. Propagated signals per se are not examples of computer storage media. Although the computer storage medium (the memory 522) is shown within the computing apparatus 518, it will be appreciated by a person skilled in the art, that the storage may be distributed or located remotely and accessed via a network or other communication link (e.g. using a communication interface 523).

The computing apparatus 518 may comprise an input/output controller 524 configured to output information to one or more output devices 525, for example a display or a speaker, which may be separate from or integral to the electronic device. The input/output controller 524 may also be configured to receive and process an input from one or more input devices 526, for example, a keyboard, a microphone or a touchpad. In one embodiment, the output device 525 may also act as the input device. An example of such a device may be a touch sensitive display. The input/output controller 524 may also output data to devices other than the output device, e.g. a locally connected printing device. In some embodiments, a user may provide input to the input device(s) 526 and/or receive output from the output device(s) 525.

The functionality described herein can be performed, at least in part, by one or more hardware logic components. According to an embodiment, the computing apparatus 518 is configured by the program code when executed by the processor 519 to execute the embodiments of the operations and functionality described. Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Program-specific Standard Products (ASSPs), System-on-a-chip systems (SOCs), Complex Programmable Logic Devices (CPLDs), Graphics Processing Units (GPUs).

At least a portion of the functionality of the various elements in the figures may be performed by other elements in the figures, or an entity (e.g., processor, web service, server, application program, computing device, etc.) not shown in the figures.

Although described in connection with an exemplary computing system environment, examples of the disclosure are capable of implementation with numerous other general purpose or special purpose computing system environments, configurations, or devices.

Examples of well-known computing systems, environments, and/or configurations that may be suitable for use with aspects of the disclosure include, but are not limited to, mobile or portable computing devices (e.g., smartphones), personal computers, server computers, hand-held (e.g., tablet) or laptop devices, multiprocessor systems, gaming consoles or controllers, microprocessor-based systems, set top boxes, programmable consumer electronics, mobile telephones, mobile computing and/or communication devices in wearable or accessory form factors (e.g., watches, glasses, headsets, or earphones), network PCs, minicomputers, mainframe computers, distributed computing environments that include any of the above systems or devices, and the like. In general, the disclosure is operable with any device with processing capability such that it can execute instructions such as those described herein. Such systems or devices may accept input from the user in any way, including from input devices such as a keyboard or pointing device, via gesture input, proximity input (such as by hovering), and/or via voice input.

Examples of the disclosure may be described in the general context of computer-executable instructions, such as program modules, executed by one or more computers or other devices in software, firmware, hardware, or a combination thereof. The computer-executable instructions may be organized into one or more computer-executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other examples of the disclosure may include different computer-executable instructions or components having more or less functionality than illustrated and described herein.

In examples involving a general-purpose computer, aspects of the disclosure transform the general-purpose computer into a special-purpose computing device when configured to execute the instructions described herein.

Alternatively, or in addition to the other examples described herein, examples include any combination of the following:
wherein the at least one network interface is further configured to communicate with at least one printer;
sends the generated digital product label to the at least one printer via the network interface;
provides the generated digital product label to a user via the at least one user interface;
wherein the at least one network interface is further configured to communicate with at least one product attribute collector device;
obtains product attribute data from the at least one product attribute collector device;
wherein receiving product identification data of the product is based on the obtained product attribute data;
wherein the obtained product attribute data is compared to stored product attribute data to identify the product identification data of the product;
wherein the obtained product attribute data is compared to stored product attribute data to validate the received product identification data;
wherein the at least one product attribute collector device includes at least one of a chemical sniffer device and an optical device;
wherein the obtained product attribute data includes at least one of chemical signature data of the product obtained by the chemical sniffer device and optical data of the product obtained by the optical device;
wherein the obtained product attribute data includes optical data, the optical data including at least one of a color of the product, a shape of the product, and an optical pattern of the product;
wherein determining product identification data of the plurality of products based on the obtained product attribute data includes comparing the optical data of the obtained product attribute data to stored optical data associated with products;
initiates a transaction based on the generated digital product label;
wherein the network interface includes at least one of a wired connection network interface, a Wi-Fi network interface, a BLUETOOTH® network interface, or a NFC network interface.
wherein the scale interface includes an optical interface configured to obtain the weight value by reading a displayed barcode including the weight value;
wherein obtaining the product value per weight data includes retrieving the product value per weight data from a cloud server upon which the product data store is stored via a network interface;
wherein receiving product identification data of a product includes obtaining product attribute data and identifying the product based on the obtained product attribute data;
obtains product attribute data from at least one product attribute collector device;
obtains stored product attribute data associated with the product from the product data store based on the received product identification data;
validates the received product identification data based on a comparison of the obtained product attribute data to the stored product attribute data;

Any range or device value given herein may be extended or altered without losing the effect sought, as will be apparent to the skilled person.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

The embodiments illustrated and described herein as well as embodiments not specifically described herein but within the scope of aspects of the claims constitute exemplary means for receiving product identification data of a product via at least one of the at least one user interface and the at least one network interface; means for obtaining product value per weight data of the product from the at least one product data store via at least one network interface; means for determining a weight value from the at least one scale device via the at least one network interface; means for calculating a product value based on the obtained product value per weight data and the determined weight value; and means for generating a digital product label including at least a portion of the product identification data and the product value. The illustrated one or more processors 519 together with the computer program code stored in memory 522 constitute exemplary processing means for generating a digital product label, including processing means for transforming and/or combining data obtained from various devices, such as scale devices and/or product attribute collector devices, in a system to create the information included in the digital product label, as described herein.

The term "comprising" is used in this specification to mean including the feature(s) or act(s) followed thereafter, without excluding the presence of one or more additional features or acts.

In some examples, the operations illustrated in the figures may be implemented as software instructions encoded on a computer readable medium, in hardware programmed or designed to perform the operations, or both. For example, aspects of the disclosure may be implemented as a system on a chip or other circuitry including a plurality of interconnected, electrically conductive elements.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of." The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A system for generating a digital product label, the system comprising:
    at least one processor;
    at least one user interface;
    at least one network interface configured to communicate with at least one scale device and at least one product data store;
    at least one memory;
    an orchestrator component, implemented on the at least one memory and executed by the processor to:
    receive product identification data of a product via at least one of the at least one user interface and the at least one network interface;
    obtain product value per weight data of the product from the at least one product data store via the at least one network interface;
    determine a weight value from the at least one scale device via the at least one network interface;
    calculate a product value based on the obtained product value per weight data and the determined weight value;
    generate a digital product label including at least a portion of the product identification data and the product value; and
    add the product identification data and the product value described on the digital product label to a virtual shopping cart of a user, wherein the digital product label is used to initiate or complete a purchase transaction for purchase of the product.

2. The system of claim 1, wherein the at least one network interface is further configured to communicate with at least one printer; and the at least one memory and computer program code are configured to, with the at least one processor, further cause the at least one processor to send the generated digital product label to the at least one printer via the network interface.

3. The system of claim 1, wherein the at least one memory and computer program code are configured to, with the at least one processor, further cause the at least one processor to provide the generated digital product label to a user via the at least one user interface.

4. The system of claim 1, wherein the at least one network interface is further configured to communicate with at least one product attribute collector device; and the at least one memory and computer program code are configured to, with the at least one processor, further cause the at least one processor to obtain product attribute data from the at least one product attribute collector device; and wherein receiving product identification data of the product is based on the obtained product attribute data.

5. The system of claim 4, wherein the obtained product attribute data is compared to stored product attribute data to identify the product identification data of the product.

6. The system of claim 4, wherein the obtained product attribute data is compared to stored product attribute data to validate the received product identification data.

7. The system of claim 4, wherein the at least one product attribute collector device includes at least one of a chemical sniffer device and an optical device; and the obtained product attribute data includes at least one of chemical signature data of the product obtained by the chemical sniffer device and optical data of the product obtained by the optical device.

8. The system of claim 7, wherein the obtained product attribute data includes optical data, the optical data including at least one of a color of the product, a shape of the product, and an optical pattern of the product.

9. The system of claim 1, wherein the at least one memory and computer program code are configured to, with the at least one processor, further cause the at least one processor to initiate a transaction based on the generated digital product label.

10. The system of claim 1, wherein the at least one memory and computer program code are configured to, with the at least one processor, further cause the at least one processor to generate the digital product label for multiple products based on product data and sequentially determined weight values for the multiple products, wherein the digital product label enables a user to purchase multiple products in one or more quantities using the same digital product label.

11. A computerized method for generating a product label, the computerized method comprising:
    obtaining, by a processor implemented on a mobile device, product attribute data associated with a plurality of products from one or more product attribute collector devices, the product attribute data associated with each product of the plurality of products received in a sequence;
    determining, by the processor, product identification data of the plurality of products based on the obtained product attribute data; obtaining, by the processor, product value per weight data of the plurality of products from a product data store via a network interface based on the determined product identification data;
    determining, by the processor, a plurality of weight values from a scale device via a scale interface in a sequence, each weight value of the plurality of weight values being associated with a product of the plurality of products based on a most recently received product identification data in the sequence of received product identification data;
    calculating, by the processor, a plurality of individual product values based on the product value per weight data of the plurality of products and the associated weight values;
    generating, by the processor, a digital product label including at least a portion of the product identification data and the plurality of individual product values;
    transmitting, by the processor, the generated digital product label to another device via a network interface; and
    adding the product identification data and the product value described on the digital product label to a virtual shopping cart of a user, wherein the digital product label is used to initiate or complete a purchase transaction for purchase of the product.

12. The computerized method of claim 11, wherein the scale interface includes an optical interface configured to determine the weight value by reading a displayed barcode including the weight value.

13. The computerized method of claim 11, wherein obtaining the product value per weight data includes retrieving the product value per weight data from a cloud server upon which the product data store is stored via the network interface.

14. The computerized method of claim 11, wherein the product attribute data includes at least one of chemical signature data obtained from a chemical sniffer sensor of a chemical sniffer device via a chemical sniffer device interface, and optical data obtained from an optical sensor of an optical device via an optical device interface.

15. The computerized method of claim 14, wherein the obtained product attribute data includes optical data, the optical data including at least one of a color of the product, a shape of the product, and an optical pattern of the product; and determining product identification data of the plurality of products based on the obtained product attribute data includes comparing the optical data of the obtained product attribute data to stored optical data associated with products.

16. The computerized method of claim 11, further comprising initiating, by the processor, a transaction based on the generated digital product label, wherein the digital product label enables a user to purchase multiple products in one or more quantities using a single digital product label.

17. One or more computer storage media having computer-executable instructions for generating a product label that, upon execution by a processor, cause the processor to at least:
    receive product identification data of a product via at least one of a user interface and a network interface;
    obtain product value per weight data of the product from a product data store via the network interface;
    determine a weight value from a scale device via a scale interface; calculate a product value based on the obtained product value per weight data and the determined weight value;
    generate a digital product label including at least a portion of the product identification data and the product value; and
    add the product identification data and the product value described on the digital product label to a virtual shopping cart of a user, wherein the digital product label is used to initiate or complete a purchase transaction for purchase of the product.

18. The one or more computer storage media of claim 17, the computer-executable instructions, upon execution by the processor, further causing the processor to at least: obtain product attribute data from at least one product attribute collector device; obtain stored product attribute data associated with the product from the product data store based on the received product identification data; and validate the received product identification data based on a comparison of the obtained product attribute data to the stored product attribute data.

19. The one or more computer storage media of claim 18, wherein the product attribute data includes at least one of chemical signature data associated with the product and optical pattern data associated with the product.

20. The one or more computer storage media of claim 17, the computer-executable instructions, upon execution by the processor, further causing the processor to at least initiate a transaction based on the generated digital product label, wherein the digital product label is generated for multiple products based on product data and sequentially determined weight values for the multiple products, wherein the digital product label enables a user to purchase multiple products in one or more quantities using a single digital product label.

* * * * *